(12) United States Patent
Everett et al.

US006384915B1

(10) Patent No.: US 6,384,915 B1
(45) Date of Patent: *May 7, 2002

(54) CATHETER GUIDED BY OPTICAL COHERENCE DOMAIN REFLECTOMETRY

(75) Inventors: Matthew Everett, Pleasanton; Billy W. Colston, Livermore; Luiz B. Da Silva, Danville; Dennis Matthews, Moss Beach, all of CA (US)

(73) Assignee: The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/050,570

(22) Filed: Mar. 30, 1998

(51) Int. Cl.[7] .............................................. G01N 15/02
(52) U.S. Cl. ....................................................... 356/336
(58) Field of Search ............................. 356/336, 338, 356/342, 115–119, 357–360, 117; 600/138, 342, 488, 561, 407, 478, 373; 606/13; 607/88; 385/116, 117, 119, 17, 24, 16, 12, 13, 15, 51; 378/51

(56) References Cited

U.S. PATENT DOCUMENTS 4,913,142 A    4/1990  Kittrell et al. ................. 606/7
5,321,501 A    6/1994  Swanson et al. ............ 356/345
5,395,361 A  * 3/1995  Fox et al.
5,512,034 A  * 4/1996  Finn et al.
5,701,371 A  * 12/1997 Ishida
6,175,669 B1 * 1/2001  Colston et al. ............... 385/12

FOREIGN PATENT DOCUMENTS

EP        0484913       5/1992
WO        WO9732182     9/1997

* cited by examiner

Primary Examiner—Frank G. Font
Assistant Examiner—Tu T. Nguyen
(74) Attorney, Agent, or Firm—Alan H. Thompson

(57) ABSTRACT

A guidance and viewing system based on multiplexed optical coherence domain reflectometry is incorporated into a catheter, endoscope, or other medical device to measure the location, thickness, and structure of the arterial walls or other intra-cavity regions at discrete points on the medical device during minimally invasive medical procedures. The information will be used both to guide the device through the body and to evaluate the tissue through which the device is being passed. Multiple optical fibers are situated along the circumference of the device. Light from the distal end of each fiber is directed onto the interior cavity walls via small diameter optics (such as gradient index lenses and mirrored corner cubes). Both forward viewing and side viewing fibers can be included. The light reflected or scattered from the cavity walls is then collected by the fibers and multiplexed at the proximal end to the sample arm of an optical low coherence reflectometer. The system may also be implemented in a nonmedical inspection device.

32 Claims, 8 Drawing Sheets

CATHETER GUIDED BY OPTICAL COHERENCE DOMAIN REFLECTOMETRY

The United States Government has rights in this invention pursuant to Contract No. W-7405-ENG-48 between the United States Department of Energy and the University of California for the operation of Lawrence Livermore National Laboratory.

BACKGROUND OF THE INVENTION

The invention relates generally to catheters and endoscopes and other inspection instruments, and more particularly to guidance and viewing systems for catheters and endoscopes and other inspection instruments.

Optical coherence domain reflectometry (OCDR) is a technique developed by Youngquist et al. in 1987 (Youngquist, R. C. et al., "Optical Coherence-Domain Reflectometry: A New Optical Evaluation Technique," 1987, Optics Letters 12(3):158–160). Danielson et al. (Danielson, B. L. et al., "Guided-Wave Reflectometry with Micrometer Resolution," 1987, Applied Physics 26(14): 2836–2842) also describe an optical reflectometer which uses a scanning Michelson interferometer in conjunction with a broadband illuminating source and cross-correlation detection. OCDR was first applied to the diagnosis of biological tissue by Clivaz et al. in January 1992 (Clivaz, X. et al., "High-Resolution Reflectometry in Biological Tissues," 1992, Optics Letters 17(1):4–6). A similar technique, optical coherence tomography (OCT), has been developed and used for imaging with catheters by Swanson et al. in 1994 (Swanson, E. A. et al., U.S. Pat. Nos. 5,321,501 and 5,459,570). Tearney et al. (Tearney, G. J. et al., "Scanning Single-Mode Fiber Optic Catheter-Endoscope for Optical Coherence Tomograph," 1996, Optics Letters 21(7):543–545) also describe an OCT system in which a beam is scanned in a circumferential pattern to produce an image of internal organs. U.S. Pat. No. 5,570,182 to Nathel et al. describes method and apparatus for detection of dental caries and periodontal disease using OCT. However, as OCT systems rely on mechanical scanning arms, miniaturizing them enough to leave room for other devices in the catheter is a serious problem.

Polarization effects in an OCDR system for birefringence characterization have been described by Hee et al. (Hee, M. R. et al., "Polarization-sensitive low-coherence reflectometer for birefringence characterization and ranging," J. Opt. Soc. Am. B, Vol. 9, No. 6, June 1992, 903–908) and in an OCT system by Everett et al. (Everett, M. J. et al., "Birefringence characterization of biological tissue by use of optical coherence tomography," Optics Letters, Vol. 23, No. 3, Feb. 1, 1998, 228–230).

In a prior art OCDR scanning system 10, shown in FIG. 1, light from a low coherence source 12 is input into a 2×2 fiber optic coupler 14, where the light is split and directed into sample arm 16 and reference arm 18. An optical fiber 20 is connected to the sample arm 16 and extends into a device 22, which scans an object 24. Reference arm 18 provides a variable optical delay. Light input into reference arm 18 is reflected back by reference mirror 26. A piezoelectric modulator 28 may be included in reference arm 18 with a fixed mirror 26, or modulator 28 may be eliminated by scanning mirror 26 in the Z-direction. The reflected reference beam from reference arm 18 and a reflected sample beam from sample arm 16 pass back through coupler 14 to detector 30 (including processing electronics), which processes the signals by techniques that are well known in the art to produce a backscatter profile (or "image") on display 32.

SUMMARY OF THE INVENTION

This invention is a device which is incorporated into a catheter, endoscope, or other medical device to measure the location, thickness, and structure of the arterial walls or other intra-cavity regions at discrete points on the medical device during minimally invasive medical procedures. The information will be used both to guide the device through the body and to evaluate the tissue through which the device is being passed. Multiple optical fibers are situated along the circumference of the device. Light from the distal end of each fiber is directed onto the interior cavity walls via small diameter optics (such as gradient index lenses and mirrored corner cubes). The light reflected or scattered from the cavity walls is then collected by the fibers which are multiplexed at the proximal end to the sample arm of an optical low coherence reflectometer. The resulting data, collected sequentially from the multiple fibers, can be used to locate small structural abnormalities in the arterial or cavity wall (such as aneurysms or arteriovenous malformations) that are currently not resolvable by existing techniques. It also provides information about branching of arteries necessary for guiding of the device through the arterial system. Since only the periphery of the catheter device is used for sensing, the central region maintains usefulness for other diagnostic or surgical instruments. This device can be incorporated into standard medical catheters, endoscopes, or other medical devices, such as surgical laser fibers, angioplasty balloons, intravascular ultra-sound probes, colonoscopes, and any other device which is traversing the body. Similarly, the invention may be implemented in non-medical inspection devices.

This invention is an optical guidance and sensing system for catheters, endoscopes and o other devices based on a multiplexed optical coherence domain reflectometer (OCDR). By multiplexing between a number of sensor fibers with an optical switch, the OCDR system of the invention has multiple sequentially accessed sensor points consisting of the tip of each multiplexed fiber. These sensor points measure the scattering of light as a function of distance from the fiber tip, thus determining both the distance between the fiber tip and the nearest tissue and any structure in that tissue.

These fibers can be placed anywhere in the catheter with their tips ending at the locations where sensing is to occur. For guiding purposes, a number of fibers could be placed in a ring around the catheter wall (or embedded in it) with their tips at the distal end of the catheter. Miniature collimating and reflection optics can be used to deflect the light from the fiber tips toward the vascular walls, thus sensing any branching of the vasculature or abnormalities in the walls.

DETAILED DESCRIPTION OF THE INVENTION

The invention uses a multiplexed optical coherence domain reflectometer in a catheter or endoscope or other tubular inspection device for guidance and for optical sensing of in vivo cavity structures during minimally invasive medical procedures or for similar exploration of nonmedical systems.

Figure 1:
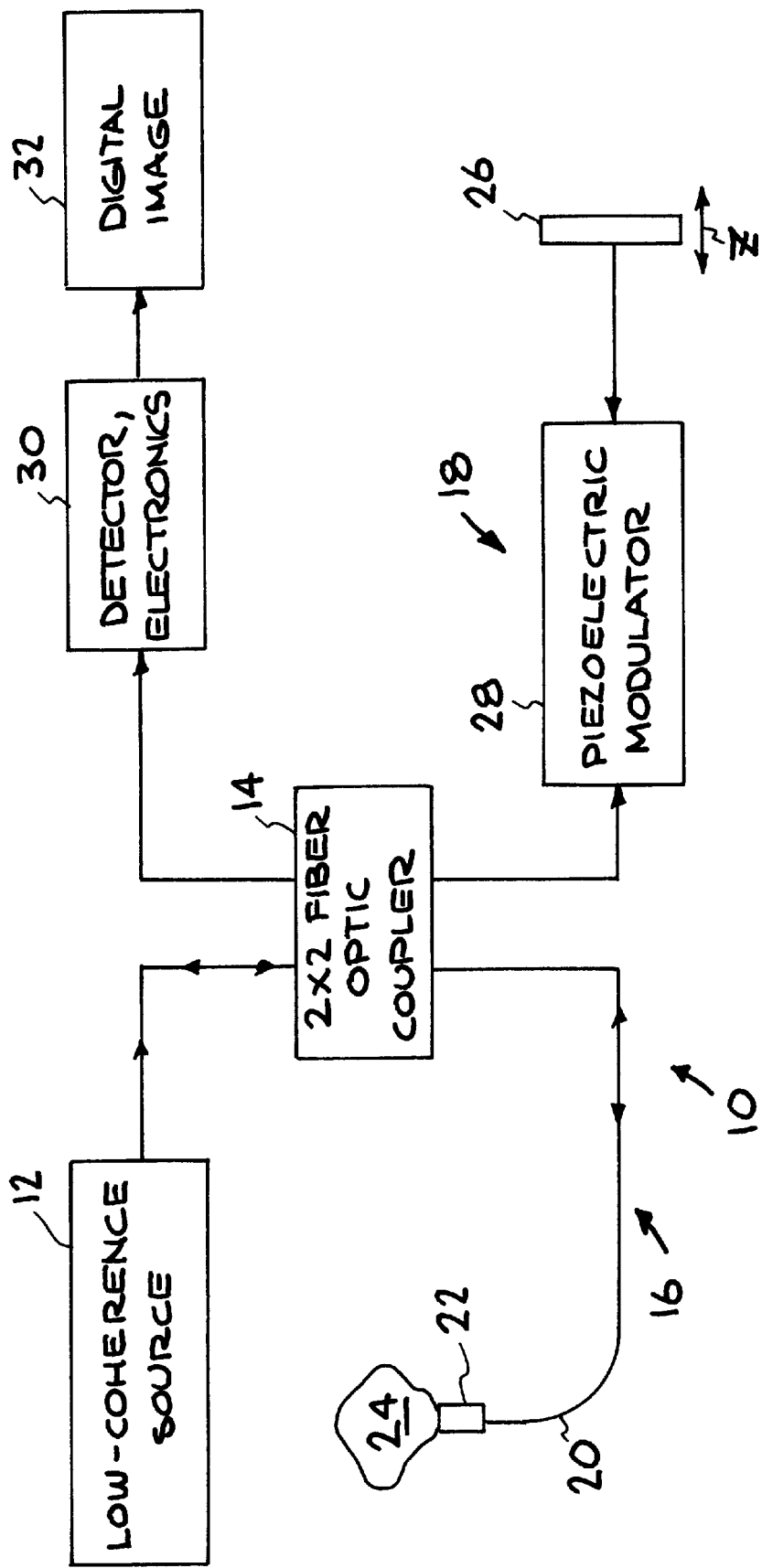
FIG. 1 is a prior art OCDR scanning system.
Figure 2A:
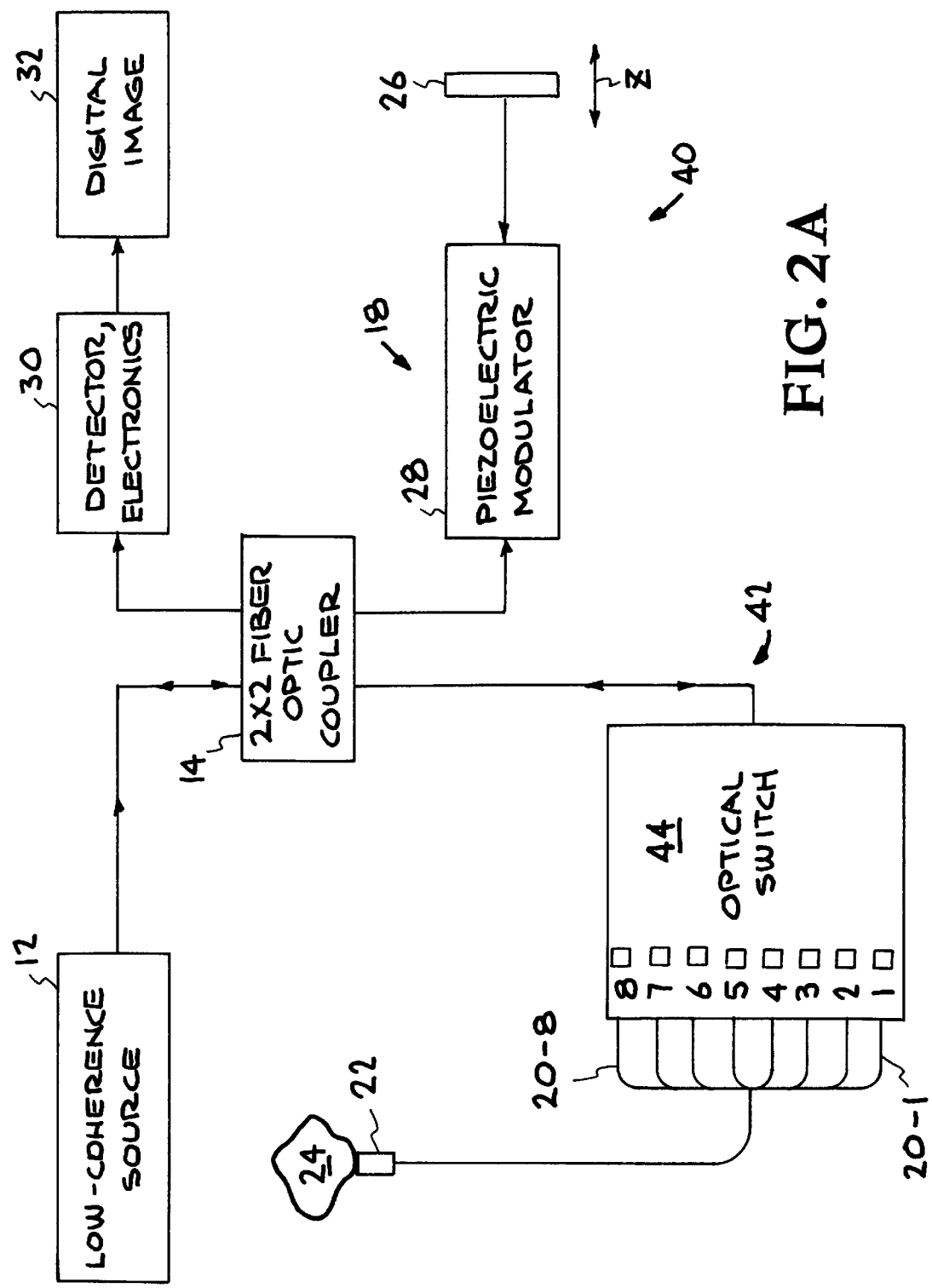
FIG. 2A is a schematic diagram of an OCDR system for catheter guidance and optical sensing with multiplexed sample arm.

The catheter/device guidance and optical sensing s system 40 is illustrated in FIG. 2A. The device is based on an optical coherence domain reflectometer (OCDR) which has been multiplexed. Except for the multiplexed feature, the system is similar to the prior art system 10 of FIG. 1. Output from a low coherence light source 12 is split at the 2×2 fiber optic coupler 14 and directed through a multiplexed sample arm 42 toward the sample 24 and through a reference arm 18 to reference mirror 26. Reflections from the mirror 26 and backscattered light from the sample 24 are recombined at the coupler 14 and propagated to the detector 30 (and light source 12). Constructive interference creates a signal at the detector 30 when the sample and reference reflections have traveled approximately the same optical group delay. The shorter the coherence length of the source, the more closely the sample and reference arm group delays must be matched for constructive interference to occur. By imposing a changing optical delay in the reference arm 18 with a known velocity, either by scanning mirror 26 in the Z-direction or with a piezomodulator 28 (with fixed mirror 26), the amplitudes and longitudinal positions of reflections from the sample 24 can be measured with high precision. The sample arm 42 contains a multiplexer 44 for switching between several (e.g., 8) optical fibers 20-1 . . . 20-8, allowing sequential spatially distinct regions to be diagnosed consecutively using the same basic OCDR system. The fibers can be placed anywhere in the device 22.

Figure 2B:
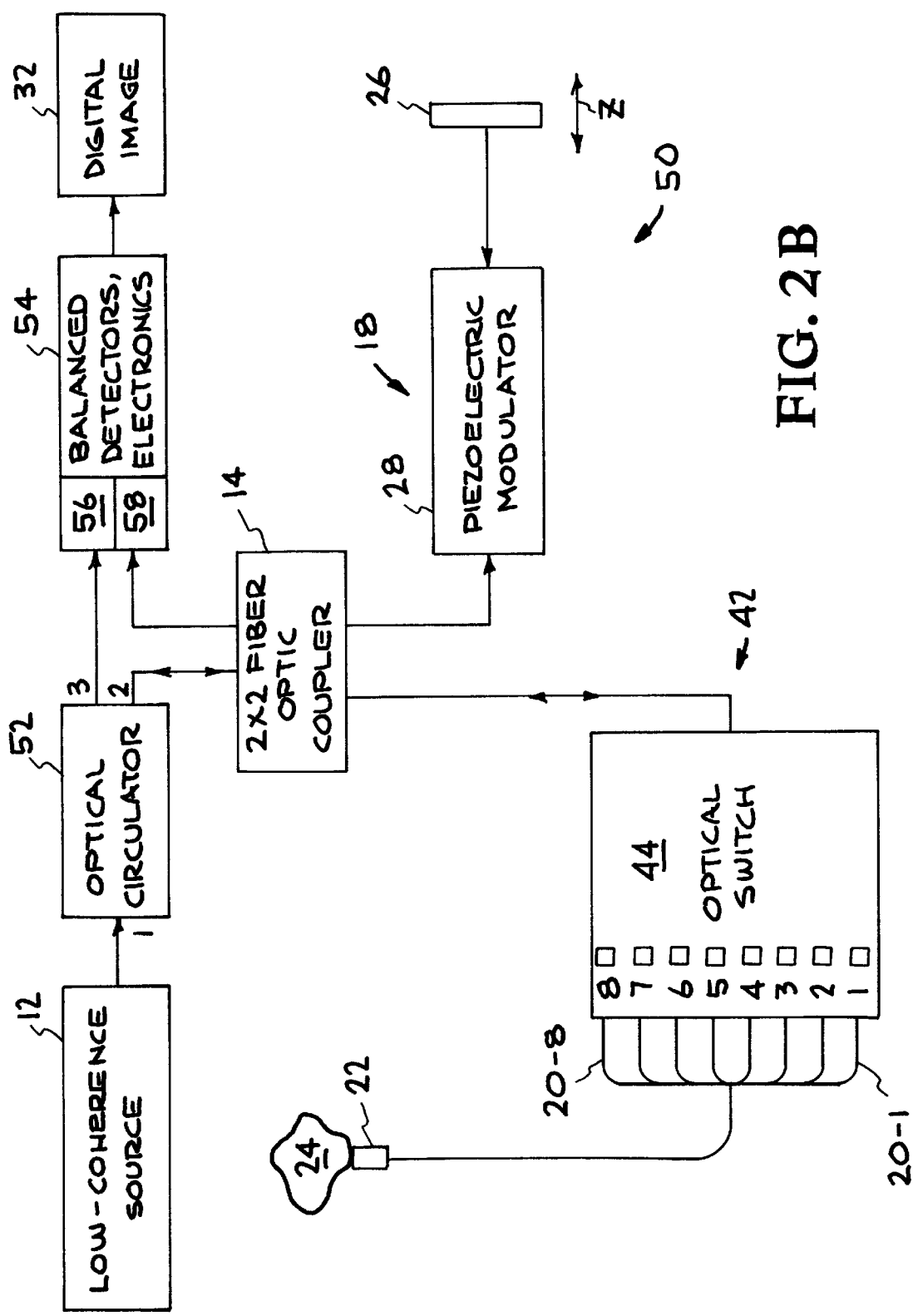
FIG. 2B is a schematic diagram of an OCDR system for catheter guidance and optical sensing with multiplexed sample arm and optical circulator.

An alternate embodiment, catheter optical sensing system 50, is shown in FIG. 2B. Catheter sensing system 50 is similar to catheter sensing system 40 of FIG. 2A, except that an optical circulator 52 is added to the system and detector 30 is replaced by balanced detector unit 54. Balanced detector unit 54 includes a pair of detectors 56, 58 with associated processing electronics and produces a backscatter profile on display 32.

OCDR/OCT systems are based on white light Michelson interferometers in which light from a source is split via a beamsplitter into two arms, a reference arm and a sample arm. Light is then reflected back to the beamsplitter in both arms. The light returning to the beamsplitter is then split, half returning to the source and the rest going to a detector. The light returning to the source is wasted and can cause the source to lase, reducing the bandwidth of the source.

The optical circulator 52 has three ports, as shown in FIG. 2B. The first port is connected to the output of source 12 and the second port is connected to coupler 14. Thus light from source 12 passes through optical circulator 52 to coupler 14 and into reference arm 18 and multiplexed sample arm 42, as before. In system 40 of FIG. 2A, the light returning to coupler 14 from reference and sample arms 18, 42 would be split, with some going to detector 30, where useful information is obtained, and some going back to source 12. In system 50 of FIG. 2B, some of the light passing back through coupler 14 goes to detector unit 54 and some goes back to the second port of optical circulator 52. But light returning to the second port of optical circulator 52 cannot pass back through the first port to source 12. Instead, the light passes through the third port to detector unit 54.

Thus putting an optical circulator 52 in the source arm between source 12 and coupler 14 allows the light that would have returned to the source 12 to be sent to another detector. Detector unit 54 contains a pair of balanced detectors 56, 58. Detector 58 receives the light which passes directly from coupler 14 while detector 56 receives the light which passes back through optical circulator 52. Thus detector unit 54 can utilize all the reflected light. In the balanced detection scheme, the signal on the second detector is subtracted from the first. The signal caused by heterodyning between light in the reference and sample arms is 180 degrees out of phase on the two detectors.

The use of optical circulator 52 provides three benefits: (1) it protects source 12 from optical back reflections which can cause it to lase; (2) it allows detector unit 54 to collect twice as much light, enhancing system sensitivity; (3) balanced detection is achieved by subtracting the signal on one detector from the other which eliminates source or ring noise as fluctuations in source intensity appear equally on both detectors and thus cancel when the two signals are subtracted.

Figure 2C:
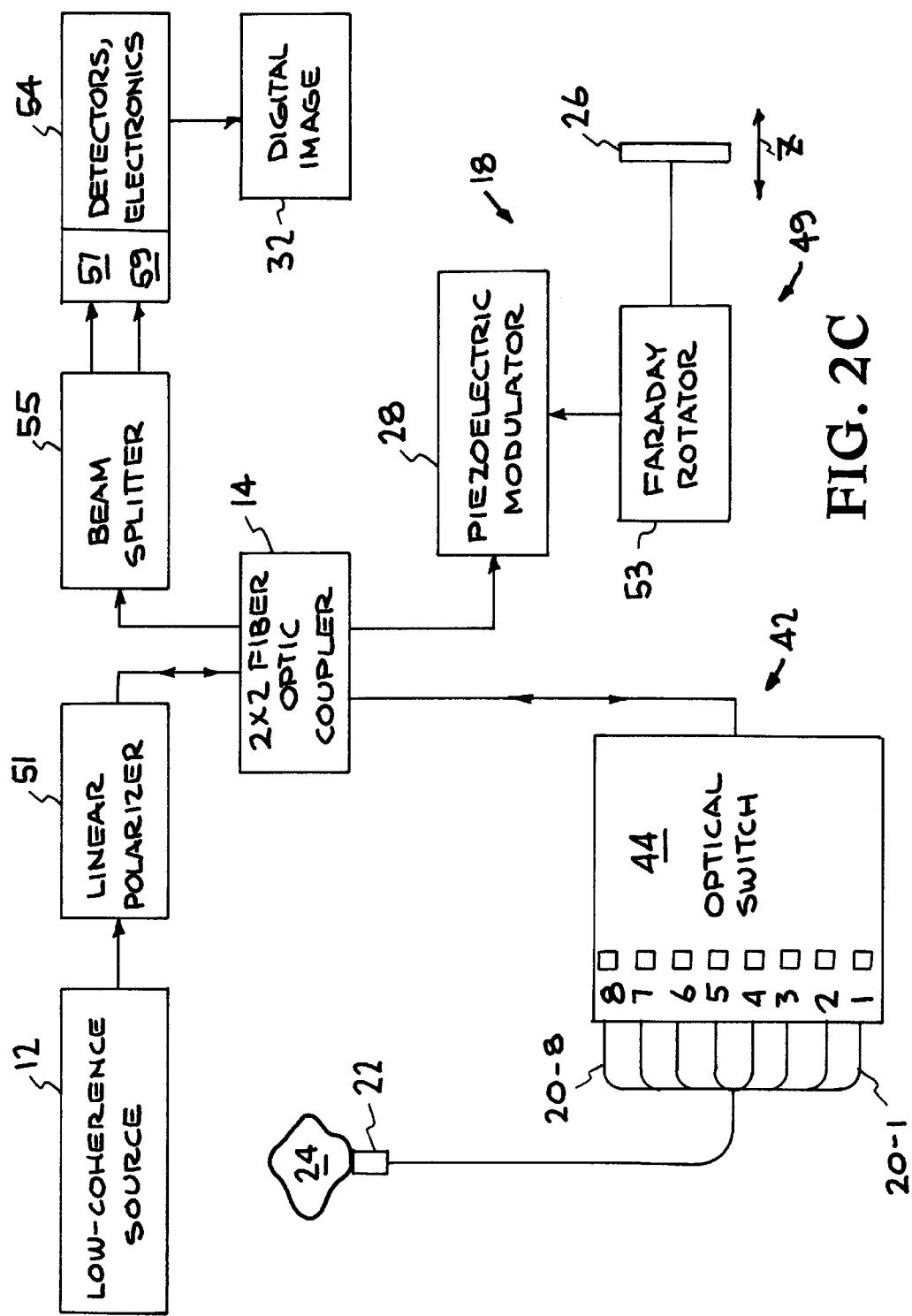
FIG. 2C is a schematic diagram of an OCDR system for catheter guidance and optical sensing with multiplexed sample arm using polarized light.

Another embodiment, catheter optical sensing system 49, is shown in FIG. 2C. Catheter sensing system 49 is similar to catheter sensing system 40 of FIG. 2A, except that the polarization of the light through the system is controlled by polarization maintaining (PM) fibers and optics. Mismatches between the polarization states of the light returning from the reference and sample arms 42, 18 in system 40 causes reduction in the coherent interference between light from the two arms and thus losses of signal. Control of the polarization state of the light in the system can both eliminate losses in signal due to depolarization of the light and provide the additional capability of measurement of the birefringence of the sample 24. In this embodiment, linearly polarized light is introduced into the system either through use of a linearly polarized broadband light source 12 or by placing linear polarizer 51 directly after an unpolarized source 12. The linear polarization of the light is then maintained through the use of PM fibers and a PM fiber optic coupler 14 where the linear polarization is one of the two modes of the PM fiber and PM coupler 14. The polarization state of the light returning from the reference arm 18 is modified by either a waveplate or faraday rotator 53 so as to be equally split between the two modes (orthogonal polarizations) of the PM fiber. A polarization beam splitter 55 in the detector arm splits the two polarizations and directs them to two separate detectors 57, 59 of detector unit 54. In one embodiment, the optical fibers 20-1 . . . 20-8 in the sample arm 42 are not polarization maintaining. In this case, the polarization beam splitter 55 ensures that the polarization state of the light from the reference and sample arms 42, 18 is matched on each detector 57, 59, thus eliminating the losses due to depolarization of the light. The light returning from the sample arm 42 is then measured by summing the signals from the two detectors 57, 59. In another embodiment, the optical fibers 20-1 . . . 20-8 in the sample arm 42 are polarization maintaining. The fibers 20-1 . . . 20-8 can be oriented such that the light leaving the fibers is linearly polarized at an angle approximately 45° relative to the fast axis of birefringence of the sample 24. Alternatively a quarter waveplate 85

(shown in FIG. 4B) can be placed at the distal end of each fiber 20-1 . . . 20-8 to cause the light entering the sample to be circularly polarized. In either case, the total light in all polarization states returning from the sample 24 is once again determined by summing the signal from the two detectors 57, 59. In addition, detector unit 54 includes means for ratioing the output signals from detectors 57, 59; the birefringence of the sample 24 is determined based on the arc tangent of the ratio of the signals from the two detectors 57, 59.

As previously described, a variable optical delay can be produced in reference arm 18 by scanning reference mirror 26 back and forth in the Z-direction (see FIGS. 1, 2A–B). However, there are two key issues in varying the axial length of the reference arm: linearity of the axial scan and duty cycle.

Figure 3A:
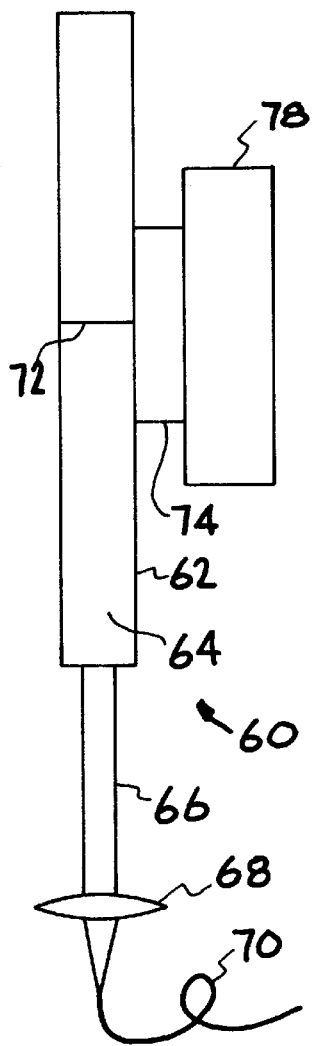
FIGS. 3A, 3B are side and top views of a rotating helix reference mirror.
Figure 3B:
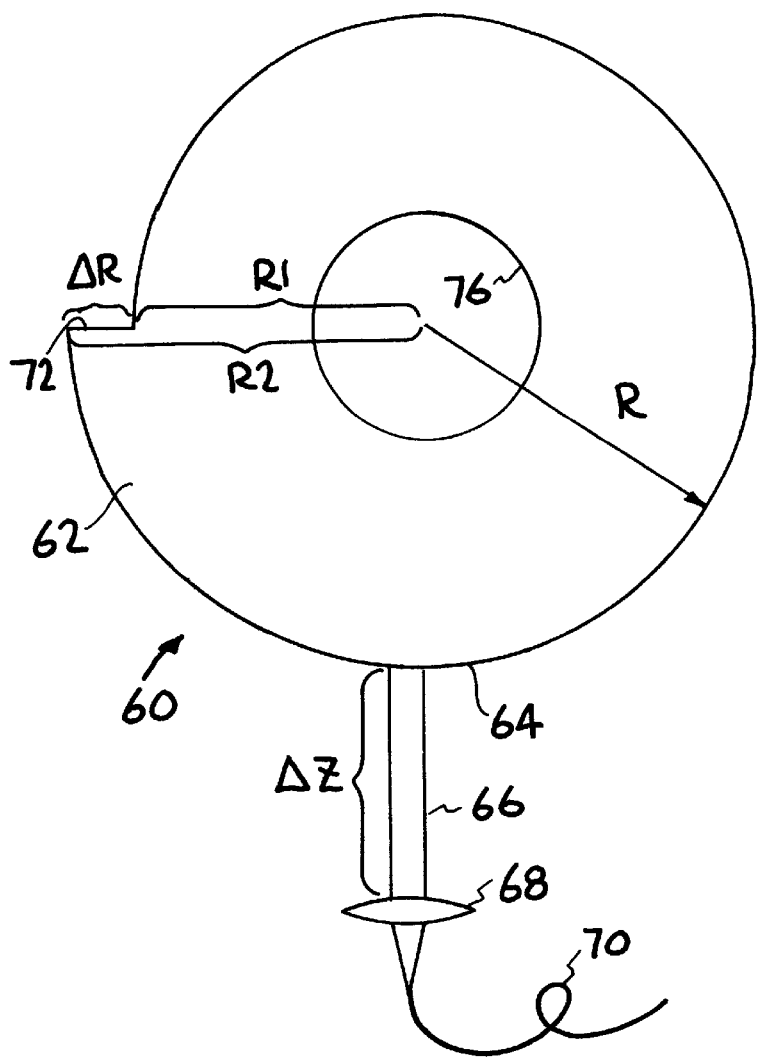

A rotating helix reference mirror 60, shown in FIGS. 3A, B, can be used to smoothly vary the path length in the reference arm of the OCDR system. Mirror 60 is formed of a disk 62 with a radius R which varies from R1 to R2 over its entire circumference. Lateral edge surface 64 of disk 62 is a highly reflective mirror so that a collimated light beam 66 incident thereon at normal incidence will be reflected back. Collimated light beam 66 is formed by collimating the diverging light from optical fiber 70, which forms the reference arm of the OCDR system. Lens 68 is used to collimate the output of fiber 70. When the beam is reflected back by surface 64, lens 68 focuses the light back into fiber 70.

When mirror 60 is positioned so that beam 66 is incident on point 72, at which the radius R=R2, the longest radius, the path length $\Delta Z$ between lens 68 and surface 64 is the shortest. As mirror 60 is rotated about shaft 74, which fits into central opening 76 and is turned by motor 78, the path length $\Delta Z$ increases as R decreases. As mirror 60 completes an entire 360 degree revolution, R=R1, the shortest radius, is reached and $\Delta Z$ has increased by $\Delta R=R2-R1$. Beam 66 then returns to point 72 and starts a new cycle. In each cycle, the path length $\Delta Z$ changes by $\Delta R$, or the optical path length change in the reference arm $\Delta L$ changes by $2\Delta Z=2\Delta R=2(R2-R1)$. Disk 62 can typically be about 2 inches in diameter and 0.2 inches thick, with a $\Delta R$ of about 0.2 inches. Thus the optical path length will be varied by about half an inch on each cycle.

Figure 4A:
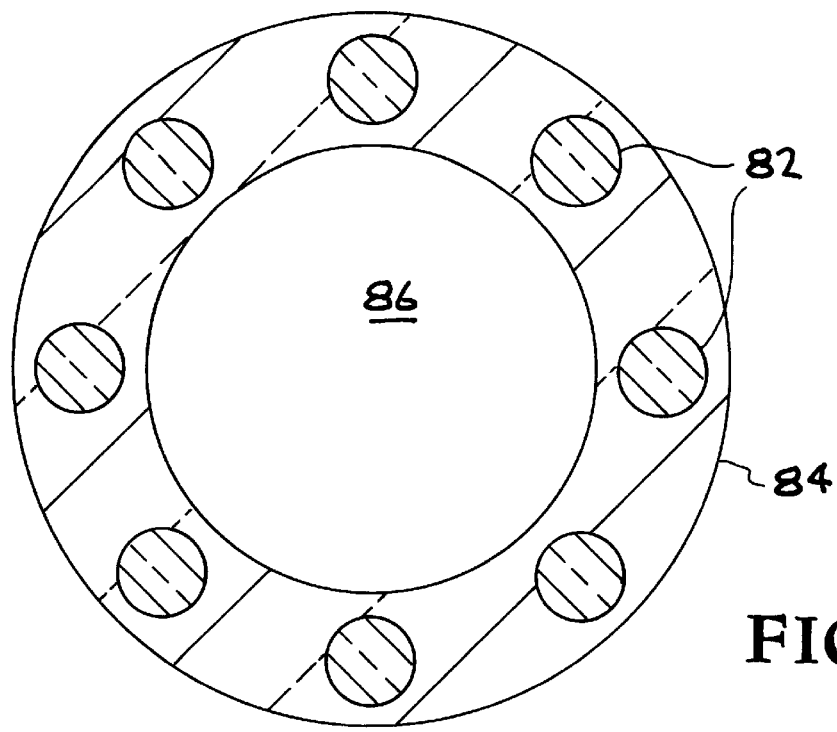
FIGS. 4A, 4B are sectional and side views of an OCDR -optical sensing catheter.
Figure 4B:
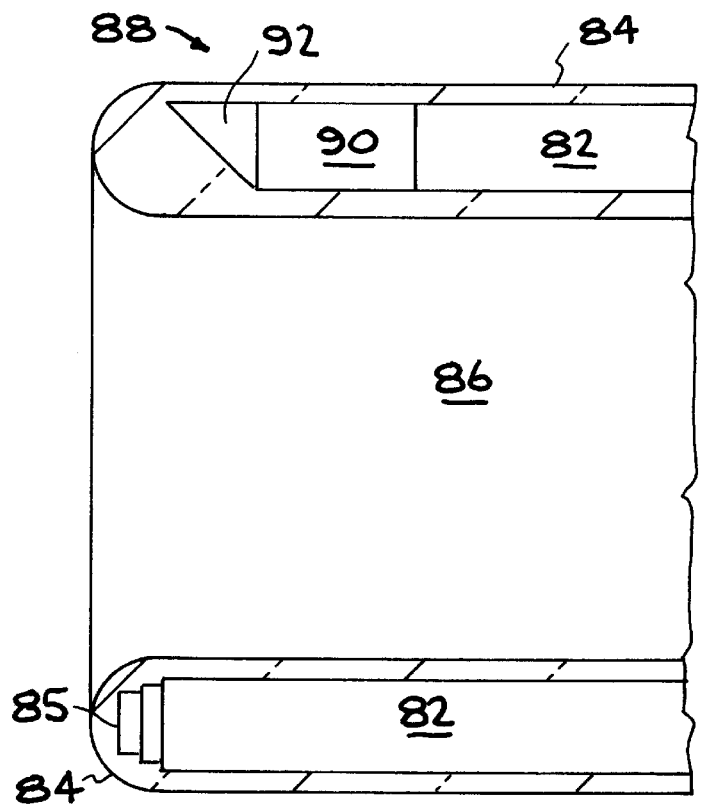

As shown in FIGS. 4A, B, the fibers 82 are embedded in plastic cover or catheter wall 84 around the circumference of the catheter or device 80 to maximize available space for other devices. The number of fibers 82 surrounding the core 86 is dependent on the limit of the device size, the fiber optic diameter, the desired speed of acquisition, and the necessary radial resolution. Either single or multiple mode optical fibers can be used. Single mode fibers are preferable for maximizing the longitudinal resolution. However, multi-mode fibers can be made smaller, thus maximizing radial resolution and catheter flexibility. Average sizes for single mode fibers are on the order of 100 $\mu$m diameter, while an average catheter is 1 to 3 mm in diameter. Thus, although eight fibers are shown in FIG. 4A, a maximum of about 30 to 100 single mode fibers could be used. Miniature optics 88, e.g. GRIN lenses 90 and mirrored corner cubes 92, as shown at the top of FIG. 4B, can be used for collimating and directing the light emerging from the fiber tips onto the arterial or cavity wall. The optical elements 88 extend through cover 84, or cover 84 is optically transparent to allow light to be transmitted to and received from the surrounding area. Miniature optics 88 can be eliminated and just the bare fiber tip can be used, as shown at the bottom of FIG. 4B; also different combinations of optical elements, e.g. GRIN lens 90 without corner cube 92 or corner cube 92 without GRIN lens 90, can also be used. Thus with different optical arrangements, forward and/or side viewing can be obtained.

Figure 5:
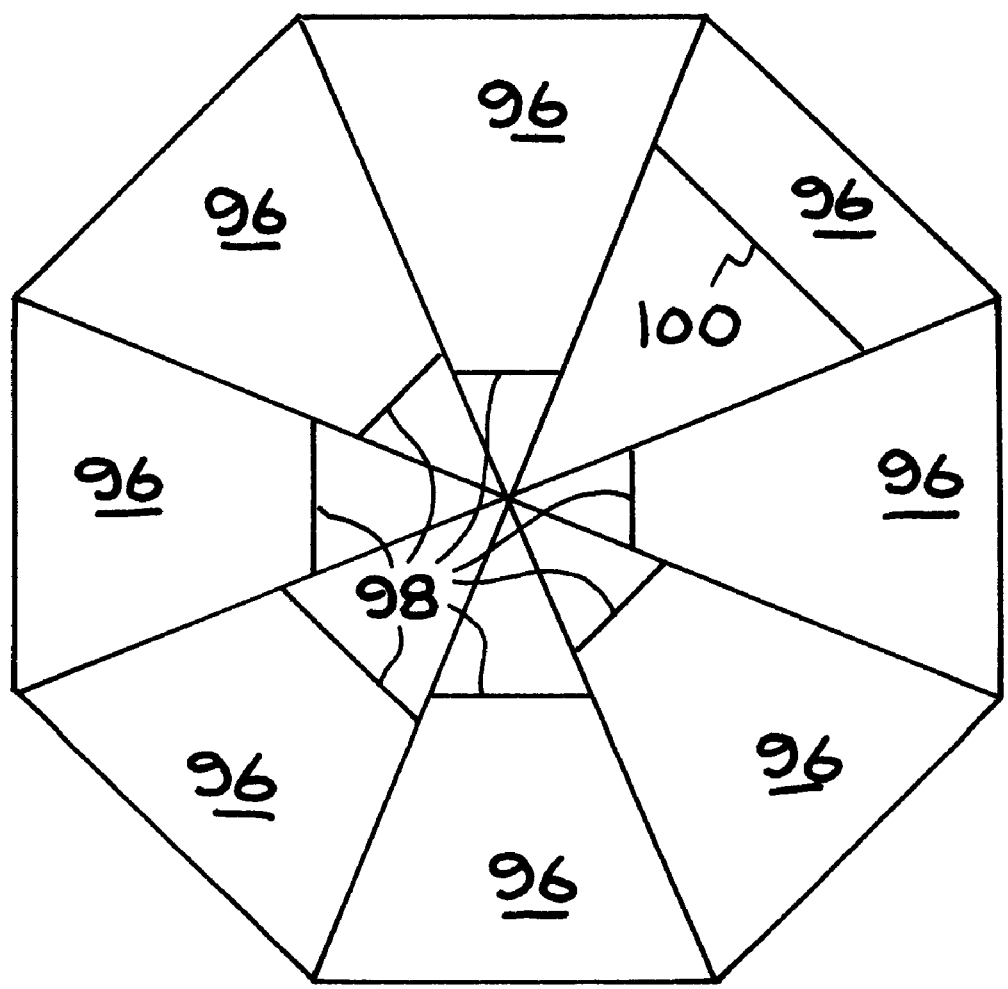
FIG. 5 is a display generated by the catheter guidance and sensing system.

The scan data can be displayed, as shown in FIG. 5, as a radial pie slice 96 for each fiber containing either a single line of data, or multiple adjoining lines portraying a history of the data collected by the fiber. Each segment 96 is the scan obtained by one of the side viewing fibers, which have been multiplexed to produce a 360 degree view. The boundaries 98 represent the artery walls. Since there are only a discrete number of fibers and-sectors 96, there are some discontinuities in the boundaries 98. However, boundary 100 is clearly much farther away and represents a junction with a secondary artery.

Figure 6:
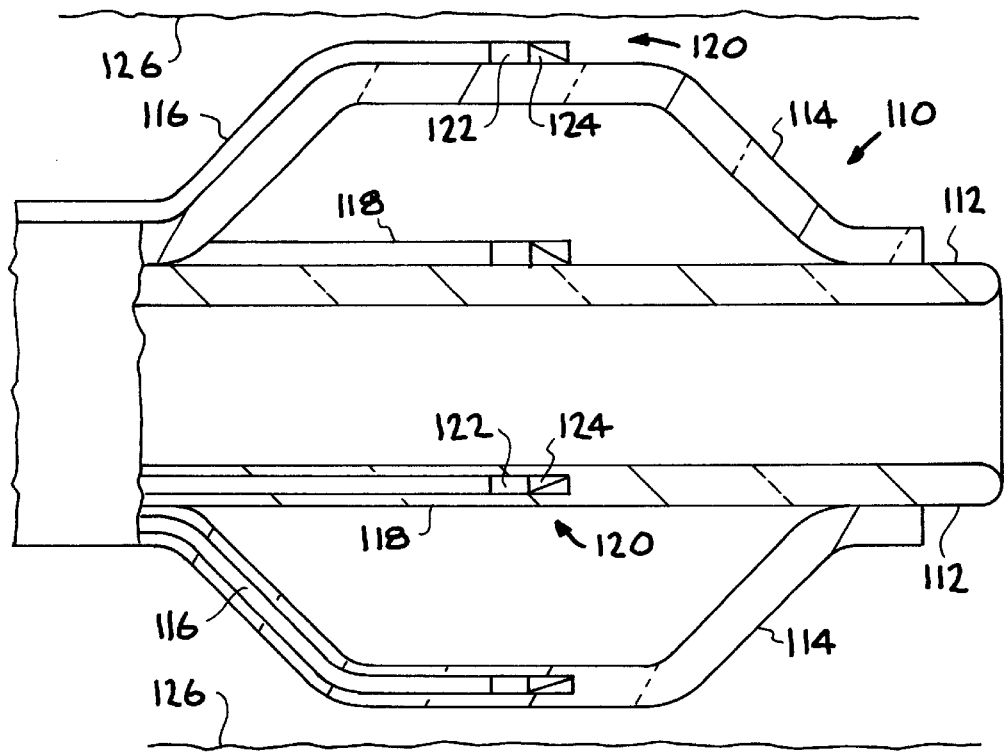
FIG. 6 shows a balloon catheter with OCDR scanning fibers.

An inflatable balloon catheter device 110 comprising a catheter tube 112 having an inflatable balloon 114 attached thereto is shown in FIG. 6. Optical fibers 116 are mounted on (as shown at top of FIG. 6) or embedded in (as shown at bottom of FIG. 6) the balloon 114. Additional fibers 118 may be mounted on (as shown at top of FIG. 6) or embedded in (as shown at bottom of FIG. 6) the catheter tube 112 inside balloon 114. By including miniature optics 120, e.g. GRIN lens 122 and corner cube 124, at the ends of fibers 116, 118, the fibers can be side viewing. Thus fibers 116 can be used to detect the arterial wall 126 while the internal fibers 118 can be used to detect the balloon 114.

Figure 7:
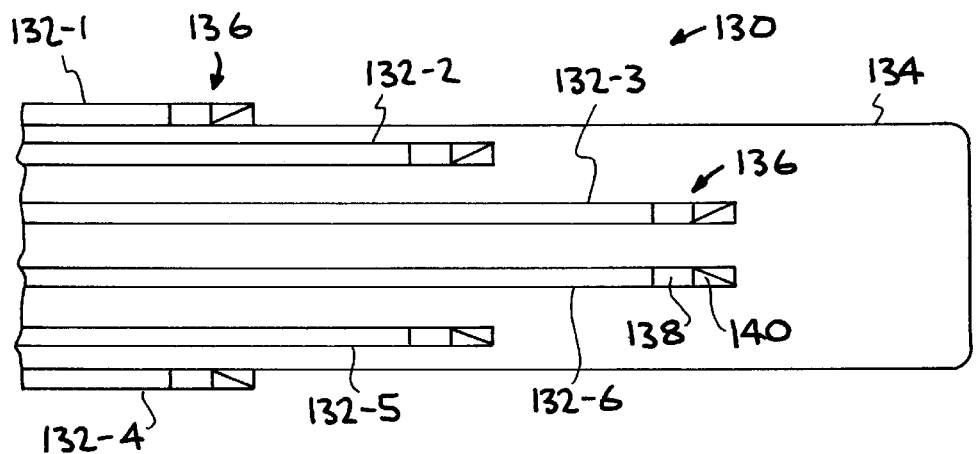
FIG. 7 shows a catheter with OCDR scanning fibers at various positions along its length.

A catheter device 130 as shown in FIG. 7 may have a plurality of fibers 132-1 . . . 132-6 mounted on (or embedded in) catheter tube 134 with individual fibers extending to different lengths along the tube 134. Each fiber may terminate in optical elements 136, e.g. GRIN lens 138 and corner cube 140, for side viewing, or some of the fibers can be forward viewing. Thus features found a different locations along the length of the catheter can be viewed without moving the catheter.

Applications for the invention include any method or procedure where accurate catheter or device positioning is beneficial, including angioplasty, stroke treatment, aneurysm, arteriovenous malformations, ophthalmic surgery, laparoscopic surgery, arthroscopic surgery, treatment of colorectal disorders, sinus disorders, ear surgery, pneumothoracic surgery, spinal surgery, bladder surgery, esophageal surgery, uteral disorders, essentially any treatment that requires accurate information about tissue structures while using a catheter or other tool inside a body cavity. In addition to medical applications, the invention can be used for non-medical instruments which can be used to inspect and probe in situ locations.

Changes and modifications in the specifically described embodiments can be carried out without departing from the scope of the invention, which is intended to be limited only by the scope of the appended claims.

What is claimed is:

1. Apparatus comprising:
   an inspection device;
   a plurality of single mode optical fibers arranged around the periphery of the inspection device, each fiber having a distal and proximal end, the fibers directing light transmitted through the fiber to a surrounding area and collecting light reflected back from the surrounding area;
   an optical coherence domain reflectometer (OCDR);
   a multiplexer connecting the OCDR to the proximal ends of the fibers to sequentially switch to each of the fibers.

2. The apparatus of claim 1 wherein the inspection device is a tubular medical device.

3. The apparatus of claim 2 wherein the tubular medical device is a catheter or endoscope.

4. The apparatus of claim 1 wherein the fibers are embedded in or mounted on a surface of a wall of the inspection device.

5. The apparatus of claim 1 wherein the inspection device is a balloon catheter comprising a catheter tube and an inflatable balloon mounted on the tube, and at least some of the fibers are mounted on the inflatable balloon.

6. The apparatus of claim 1 further comprising optical elements connected to the distal ends of at least some of the fibers.

7. The apparatus of claim 6 wherein the optical elements comprise a graded index lens and a corner cube at the distal ends of the fibers.

8. The apparatus of claim 1 wherein some fibers are forward viewing and some fibers are side viewing.

9. The apparatus of claim 1 wherein the distal ends of at least some of the fibers are positioned at different lengths along the inspection device.

10. The apparatus of claim 1 wherein the OCDR comprises:
    a 2×2 fiber optic coupler having first, second, third, and fourth ports;
    a low coherence source connected to the first port;
    the multiplexer being connected to the second port;
    a reference arm connected to the third port;
    a detector unit connected to the fourth port.

11. The apparatus of claim 10 further comprising a display device connected to the detector unit.

12. The apparatus of claim 10 further comprising an optical circulator connected between the source and the first port of the coupler and also connected to the detector unit.

13. The apparatus of claim 12 wherein the detector unit comprises a pair of balanced detectors, one detector being connected to the optical circulator and the other detector being connected to the fourth port of the coupler.

14. The apparatus of claim 10 wherein the reference arm comprises a scanning reference mirror.

15. The apparatus of claim 14 wherein the scanning reference mirror comprises a rotating helix reference mirror.

16. The apparatus of claim 15 wherein the rotating helix reference mirror comprises a disk with a radius which varies from a first radius to a second radius over its entire circumference, and having a mirror surface around its circumference.

17. The apparatus of claim 10 wherein the reference arm comprises a piezomodulator and a stationary reference mirror.

18. The apparatus of claim 10 wherein the optical fibers are polarization maintaining (PM) fibers and the coupler is a PM coupler.

19. The apparatus of claim 18 wherein the source is a linearly polarized light source or an unpolarized light source and a linear polarizer following the source.

20. The apparatus of claim 19 further comprising a waveplate or faraday rotator in the reference arm.

21. The apparatus of claim 20 wherein the detector unit comprises a pair of detectors, and further comprising a polarization beamsplitter positioned before the detectors to split returning light into two orthogonal polarizations, each polarization being input into a corresponding detector.

22. The apparatus of claim 21 wherein the detector unit includes means for determining birefringence versus depth of a sample by ratioing output signals from the pair of detectors.

23. The apparatus of claim 22 wherein linearly polarized light in the sample arm is directed into a birefringent sample with its axis of polarization at about 45 degrees relative to the fast axis of the sample.

24. The apparatus of claim 22 further comprising a quarter wave plate placed at the distal end of each of the fibers to cause light incident onto the sample to be circularly polarized.

25. The apparatus of claim 1 wherein the fibers are side viewing.

26. Apparatus comprising:
    an inspection device;
    a plurality of optical fibers arranged around the periphery of the inspection device, each fiber having a distal and proximal end, the fibers directing light transmitted through the fiber to a surrounding area and collecting light reflected back from the surrounding area;
    an optical coherence domain reflectometer (OCDR) comprising a 2×2 fiber optic coupler having first, second, third, and fourth ports;
    a low coherence source connected to the first port;
    the multiplexer being connected to the second port;
    a reference arm connected to the third port;
    a detector unit connected to the fourth port; and
    an optical circulator connected between the source and the first port of the coupler and also connected to the unit; and
    a multiplexer connecting the OCDR to the proximal ends of the fibers to sequentially switch to each of the fibers.

27. The apparatus of claim 26 wherein the detector unit comprises a pair of balanced detectors, one detector being connected to the optical circulator and the other detector being connected to the fourth port of the coupler.

28. The apparatus of claim 26 further comprising a display device connected to the detector unit.

29. Apparatus comprising:
    an inspection device;
    a plurality of optical fibers arranged around the periphery of the inspection device, each fiber having a distal and proximal end, the fibers directing light transmitted through the fiber to a surrounding area and collecting light reflected back from the surrounding area, the optical fibers are polarization maintaining (PM) fibers;
    an optical coherence domain reflectometer (OCDR) comprising a 2×2 fiber optic PM coupler having first, second, third, and fourth ports;
    a low coherence source connected to the first port wherein the source is a linearly polarized light source or an unpolarized light source and a linear polarizer following the source;
    the multiplexer being connected to a second port;
    a reference arm comprising a waveplate or faraday rotator connected to the third port;
    a detector unit comprising a pair of detectors connected to the fourth port and further comprising a polarization beamsplitter positioned before the detectors to split returning light into two orthogonal polarizations, each polarization being input into a corresponding detector; and a multiplexer connecting the OCDR to the proximal ends of the fibers to sequentially switch to each of the fibers.

30. The apparatus of claim 29 wherein the detector unit includes means for determining birefringence versus depth of a sample by ratioing output signals from the pair of detectors.

31. The apparatus of claim 30 wherein linearly polarized light in the sample arm is directed into a birefringent sample with its axis of polarization at about 45° relative to the fast axis of the sample.

32. The apparatus of claim 30 further comprising a quarter wave plate placed at the distal end of each of the fibers to cause light incident onto the sample to be circularly polarized.

* * * * *